(12) United States Patent
Zuluaga et al.

(10) Patent No.: US 7,426,410 B2
(45) Date of Patent: Sep. 16, 2008

(54) SPECTROSCOPY OF DEEPLY-SCATTERED LIGHT

(75) Inventors: Andres Zuluaga, Boston, MA (US); Stephen Dejesus, Newton, MA (US)

(73) Assignee: InfraReDx, Inc., Burlington, MA (US)

( * ) Notice: Subject to any disclaimer, the term of this patent is extended or adjusted under 35 U.S.C. 154(b) by 677 days.

(21) Appl. No.: 10/456,979

(22) Filed: Jun. 6, 2003

(65) Prior Publication Data

US 2004/0249289 A1    Dec. 9, 2004

(51) Int. Cl.
*A61B 6/00* (2006.01)
(52) U.S. Cl. .................. 600/476; 600/473; 600/478; 600/407; 600/477
(58) Field of Classification Search ......... 600/309–344, 600/473–480, 407, 408; 606/1–19
See application file for complete search history.

(56) References Cited

U.S. PATENT DOCUMENTS

| | | | | |
|---|---|---|---|---|
| 3,818,902 A * | 6/1974 | Kinoshita et al. | ........... | 600/109 |
| 4,195,904 A * | 4/1980 | Yamashita | .................. | 359/367 |
| 4,718,417 A * | 1/1988 | Kittrell et al. | .................. | 606/7 |
| 5,190,028 A | 3/1993 | Lafferty et al. | | |
| 5,192,278 A * | 3/1993 | Hayes et al. | .................. | 606/15 |
| 5,195,968 A * | 3/1993 | Lundquist et al. | ......... | 604/95.04 |
| 5,452,723 A * | 9/1995 | Wu et al. | ..................... | 600/342 |
| 5,496,305 A * | 3/1996 | Kittrell et al. | .................. | 606/15 |
| 5,813,987 A * | 9/1998 | Modell et al. | .................. | 600/473 |
| 6,134,003 A * | 10/2000 | Tearney et al. | ............... | 356/479 |
| 6,364,830 B1 | 4/2002 | Durell | | |
| 6,564,088 B1 | 5/2003 | Soller et al. | .................. | 600/478 |
| 6,571,118 B1 * | 5/2003 | Utzinger et al. | ............. | 600/476 |
| 6,654,630 B2 * | 11/2003 | Zuluaga et al. | ............... | 600/476 |
| 6,816,743 B2 * | 11/2004 | Moreno et al. | ............... | 600/473 |
| 2002/0045811 A1 | 4/2002 | Kittrell et al. | | |
| 2002/0183622 A1 | 12/2002 | Zuluaga et al. | | |

OTHER PUBLICATIONS

International Search Report, PCT/US2004/016768, mailed on Oct. 4, 2004, 11 pages.

* cited by examiner

*Primary Examiner*—Brian Casler
*Assistant Examiner*—Sanjay Cattungal
(74) *Attorney, Agent, or Firm*—Fish & Richardson P.C.

(57) ABSTRACT

A spectroscope includes first and second beam redirectors in optical communication with first and second fibers respectively. The first and second beam redirectors are oriented to illuminate respective first and second areas. The second area is separated from the first area by a separation distance that exceeds the separation distance between the first and second beam redirectors.

29 Claims, 9 Drawing Sheets

SPECTROSCOPY OF DEEPLY-SCATTERED LIGHT

FIELD OF INVENTION

The invention relates to spectroscopy, and in particular, to spectroscopes for detecting vulnerable plaques within a wall of a blood vessel.

BACKGROUND

Atherosclerosis is a vascular disease characterized by a modification of the walls of blood-carrying vessels. Such modifications, when they occur at discrete locations or pockets of diseased vessels, are referred to as plaques. Certain types of plaques are associated with acute events such as stroke or myocardial infarction. These plaques are referred to as "vulnerable plaques." A vulnerable plaque typically includes a lipid-containing pool of necrotic debris separated from the blood by a thin fibrous cap. In response to elevated intraluminal pressure or vasospasm, the fibrous cap can become disrupted, exposing the contents of the plaque to the flowing blood. The resulting thrombus can lead to ischemia or to the shedding of emboli.

One method of locating vulnerable plaque is to peer through the arterial wall with infrared light. To do so, one inserts a catheter through the lumen of the artery. The catheter includes a delivery fiber that sends infrared light to a delivery mirror. Infrared light reflects off the delivery mirror toward a spot on the arterial wall. Some of this infrared light penetrates the wall, scatters off structures within the arterial wall, and re-enters the lumen. This re-entrant light falls on a collection mirror, which then guides it to a collection fiber. The collection mirror and the delivery mirror are separated from each other by a gap. Because the catheter must be narrow enough to fit through blood vessels, the collection mirror and the delivery mirror are typically separated in the axial direction.

To a great extent, the separation between the delivery mirror and the collection mirror controls the depth from which most of the light gathered by the collection mirror is scattered. To gather more light from scattered from deep within the wall, one increases the gap between the collection mirror and the delivery mirror.

The collection mirror and the delivery mirror are mounted in a rigid housing at the distal tip of the catheter. To enable the catheter to negotiate sharp turns, it is desirable for the rigid housing to be as short as possible. This places an upper limit on the extent of the gap between the two mirrors, and hence an upper limit on the depth from which scattered light can be gathered.

SUMMARY

The invention is based on the recognition that one can increase the effective separation distance between a collection-beam redirector and a delivery-beam redirector by controlling the directions in which those redirectors direct light.

In one aspect, the invention provides a spectroscope having first and second fibers. First and second beam redirectors are in optical communication with the first and second fibers respectively. The first and second beam redirectors are oriented to illuminate respective first and second areas. The second area is separated from the first area by a separation distance that exceeds a separation distance between the first and second beam redirectors.

In one embodiment, the first beam redirector includes a mirror. However, the first beam redirector can also be a lens system or a diffracting element. Alternatively, by bending the first fiber to illuminate the first area, the first beam redirector becomes the distal end of the first fiber.

In another embodiment, the extent to which the second separation distance exceeds the separation distance between the first and second beam redirectors is chosen to enhance collection of light scattered from a target located at a selected distance from the first area.

In another aspect, the invention provides a method for collecting light scattered from behind an arterial wall by illuminating an illumination spot on the arterial wall, pointing a collection-beam redirector away from the illumination spot, and recovering scattered light incident on the collection-beam redirector.

In some practices of the invention, pointing a collection-beam redirector includes orienting a collection mirror to collect light from a direction away from the illumination spot. In other practices of the invention, pointing a collection beam redirector includes providing a lens to direct light received from a direction away from the illumination spot, or orienting an end of an optical fiber to receive light from a direction away from the illumination spot.

In other practices of the invention, pointing a collection-beam redirector includes selecting a depth from which to receive the scattered light, and pointing the collection-beam redirector in a direction that enhances the amount of light received from that depth.

Another aspect of the invention provides a method for collecting light scattered from behind an arterial wall. This method includes pointing a collection-beam redirector at a collection spot on the wall, pointing a delivery-beam redirector at the wall in a direction away from the collection spot, passing light through the delivery-beam redirector, and recovering scattered light incident on the collection-beam redirector.

In some practices of the invention, pointing a delivery-beam redirector includes orienting a delivery mirror to direct light along a direction away from the collection spot. Other practices include pointing a delivery-beam redirector by providing a lens to direct light along a direction away from the collection spot, or by orienting an end of an optical fiber to direct light along a direction away from the collection spot.

In yet other practices, the method includes selecting a depth from which to collect the scattered light, and pointing the delivery-beam redirector in a direction that enhances the amount of light received from the selected depth.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

System Overview

Figure 1:
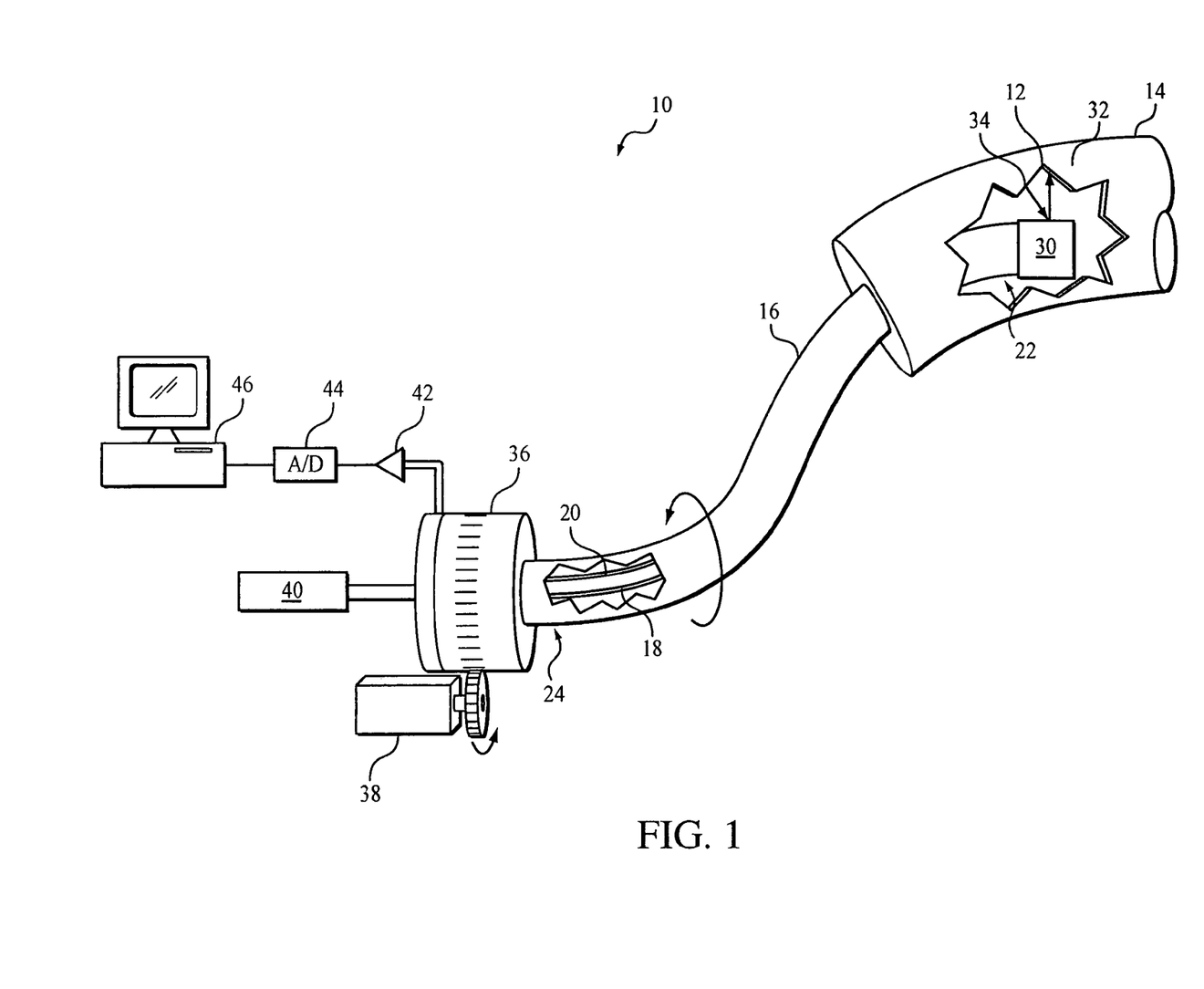
FIG. 1 is a schematic of a system for identifying vulnerable plaque in a patient.

FIG. 1 shows a diagnostic system 10 for identifying vulnerable plaque 12 in an arterial wall 14 of a patient. The diagnostic system features a catheter 16 to be inserted into a selected artery, e.g. a coronary artery, of the patient. A delivery fiber 18 and a collection fiber 20 extend between a distal end 22 and a proximal end 24 of the catheter 16.

Figure 2:
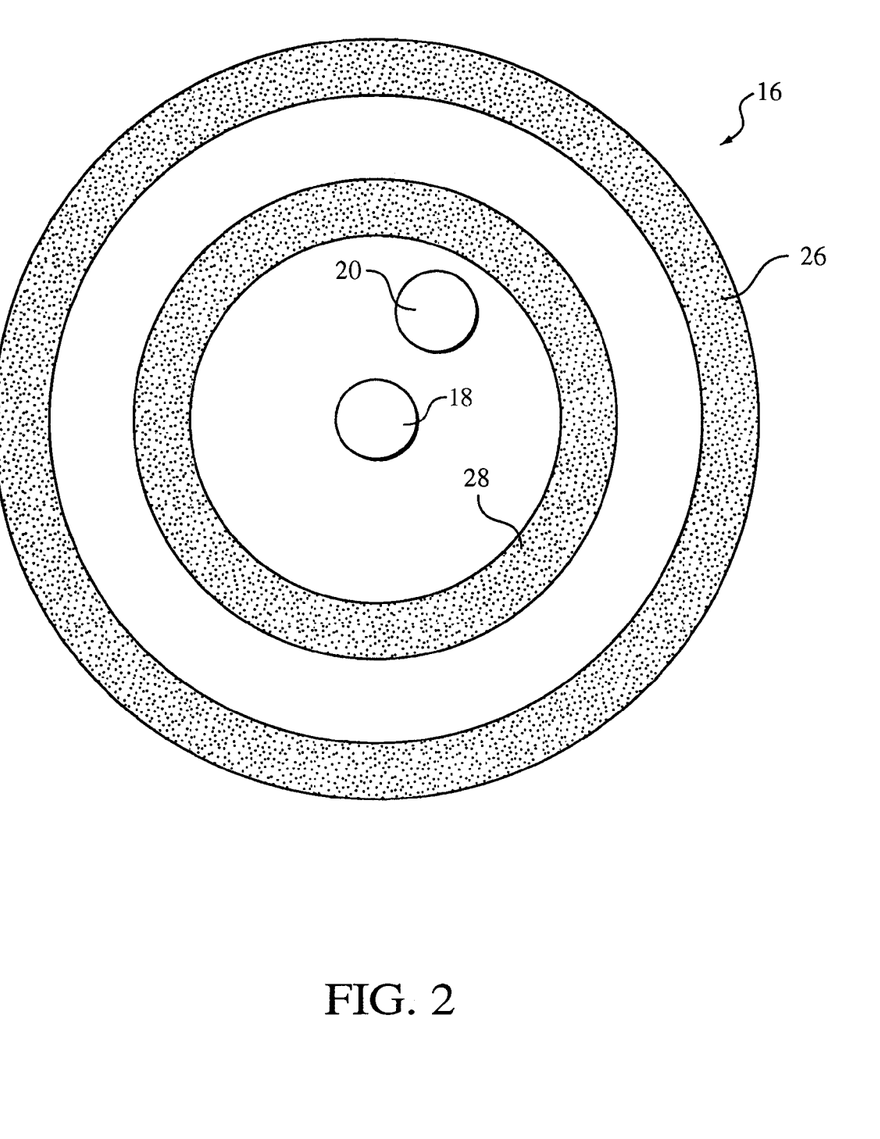
FIG. 2 is a cross-section of the catheter in FIG. 1.

As shown in FIG. 2, the catheter 16 includes a sheath 26 surrounding a rotatable torque cable 28. The delivery fiber 18 extends along the center of a torque cable 28, and the collection fiber 20 extends parallel to, but radially displaced from, the delivery fiber 18. The rotatable torque cable 28 spins at a rate between approximately 1 revolution per second and 400 revolutions per second.

At the distal end 21 of the catheter 16, a tip assembly 30 coupled to the torque cable 28 directs light traveling axially on the delivery fiber 18 toward an illumination spot 32 on the arterial wall 14. The tip assembly 30 also collects light from a collection spot 34 on the arterial wall 14 and directs that light into the collection fiber 20.

The tip assembly 30 is typically a rigid housing that is transparent to infra-red light. To enable the catheter 16 to negotiate turns as it traverses the vasculature, it is desirable for the tip assembly 30 to extend only a short distance in the axial direction.

A multi-channel coupler 36 driven by a motor 38 engages the proximal end 24 of the torque cable 28. When the motor 38 spins the multi-channel coupler 36, both the coupler 36, the torque cable 28, and the tip assembly 30 spin together as a unit. This feature enables the diagnostic system 10 to circumferentially scan the arterial wall 14 with the illumination spot 32.

In addition to spinning the torque cable 28, the multi-channel coupler 36 guides light from a laser 40 (or other light source such as a light-emitting diode, a super-luminescent diode, or an arc lamp) into the delivery fiber 18 and guides light emerging from the collection fiber 20 into one or more detectors (not visible in FIG. 1).

The detectors provide an electrical signal indicative of light intensity to an amplifier 42 connected to an analog-to-digital ("A/D") converter 44. The A/D converter 44 converts this signal into digital data that can be analyzed by a processor 46 to identify the presence of a vulnerable plaque 12 hidden beneath the arterial wall 14.

Optical Bench

Figure 3:
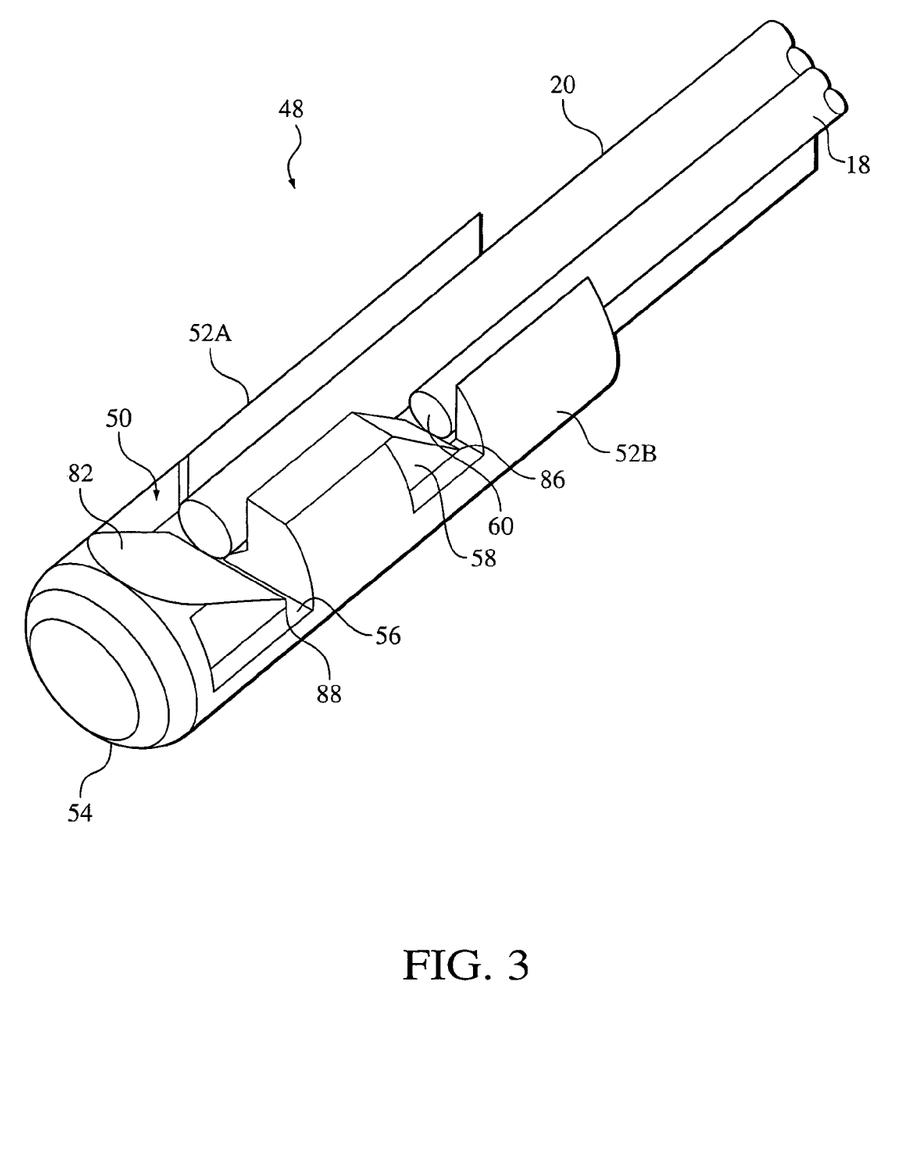
FIG. 3 is a view of an optical bench at the tip assembly of the catheter in FIG. 1.

FIG. 3 shows an optical bench 48 in which are seated the collection fiber 20 and the delivery fiber 18. The optical bench 48 is seated in a recess 50 between first and second side walls 52A-B of the distal end of a housing 54. The housing 54 is in turn coupled to the distal end of the torque cable 28. The recess 50 is just wide enough to enable the collection fiber 20 and the delivery fiber 18 to nestle adjacent to each other. A floor 56 extending between the first and second side walls 52A-B and across the recess 50 supports both the collection and delivery fibers 18, 20.

Just distal to the end of the delivery fiber 18, a portion of the optical bench 48 forms a frustum 58. The frustum 58 extends transversely only half-way across the optical bench 48, thereby enabling the collection fiber 20 to extend distally past the end of the delivery fiber 18.

The frustum 58 has an inclined surface facing the distal end of the delivery fiber 18 and a vertical surface facing the distal end of the optical bench 48. The inclined surface forms a 135 degree angle relative to the floor 56. However, other angles can be selected depending on the direction in which light from the delivery fiber 18 is to be directed. A reflective material coating the inclined surface forms a beam redirector, which in this case is a delivery mirror 60. When light exits axially from the delivery fiber 18, the delivery mirror 60 intercepts that light and redirects it radially outward to the arterial wall 14. Examples of other beam redirectors include prisms, lenses, diffraction gratings, and combinations thereof.

The collection fiber 20 extends past the end of the delivery fiber 18 until it terminates at a plane that is coplanar with the vertical face of the frustum 58. Just beyond the distal end of the collection fiber 20, a portion of the optical bench 48 forms an inclined surface extending transversely across the optical bench 48 and making an angle greater than 135 degrees relative to the floor 56. A reflective material coating the inclined surface forms a collection mirror 82.

A delivery-fiber stop 86 molded into the optical bench 48 proximal to the frustum 58 facilitates placement of the delivery fiber 18 at a desired location proximal to the delivery mirror 60. Similarly, a collection-fiber stop 88 molded into the optical bench 48 just proximal to the collection mirror 82 facilitates placement of the collection fiber 20 at a desired location proximal to the collection mirror 82.

Spatial Distribution of Scattered Light

Figure 4:
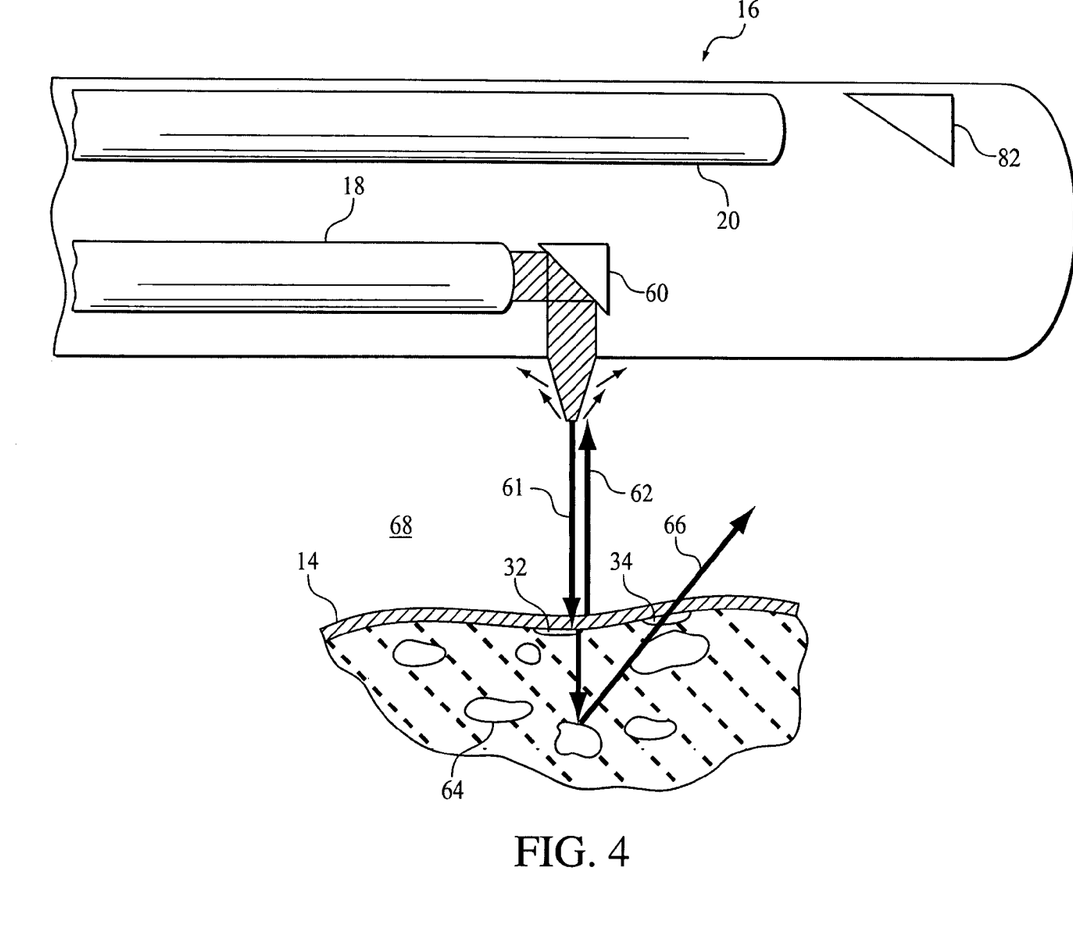
FIG. 4 is a schematic of the paths traveled by light from the delivery fiber of FIG. 1.

Referring to FIG. 4, light travels radially outward from the delivery mirror 60 toward the illumination spot 32 on the arterial wall 14. As the light does so, it encounters the blood that fills a lumen 68. Because of scattering by particles in the blood, many photons never reach the wall 14. This loss of energy is shown schematically by a progressive narrowing of the beam as it nears the wall 14. The remaining photons 61 eventually reach the arterial wall 14. Some of these photons are reflected from the wall 14. These specularly reflected photons 62 carry little or no information about structures 64 behind the arterial wall 14 and are therefore of little value. Of those photons 63 that penetrate the wall, many others are absorbed. The remainder 66 are scattered by structures 64 behind the wall 14. After having been scattered, a few of these remaining photons 66 again pass through the arterial wall 14 and re-enter the lumen 68. This remnant of the light 61 originally incident on the wall, which is referred to herein as the "re-entrant light 66," carries considerable information about the structures 64 behind the arterial wall 14. It is therefore this re-entrant light 66 that is to be guided into the collection fiber 20.

Figure 5:
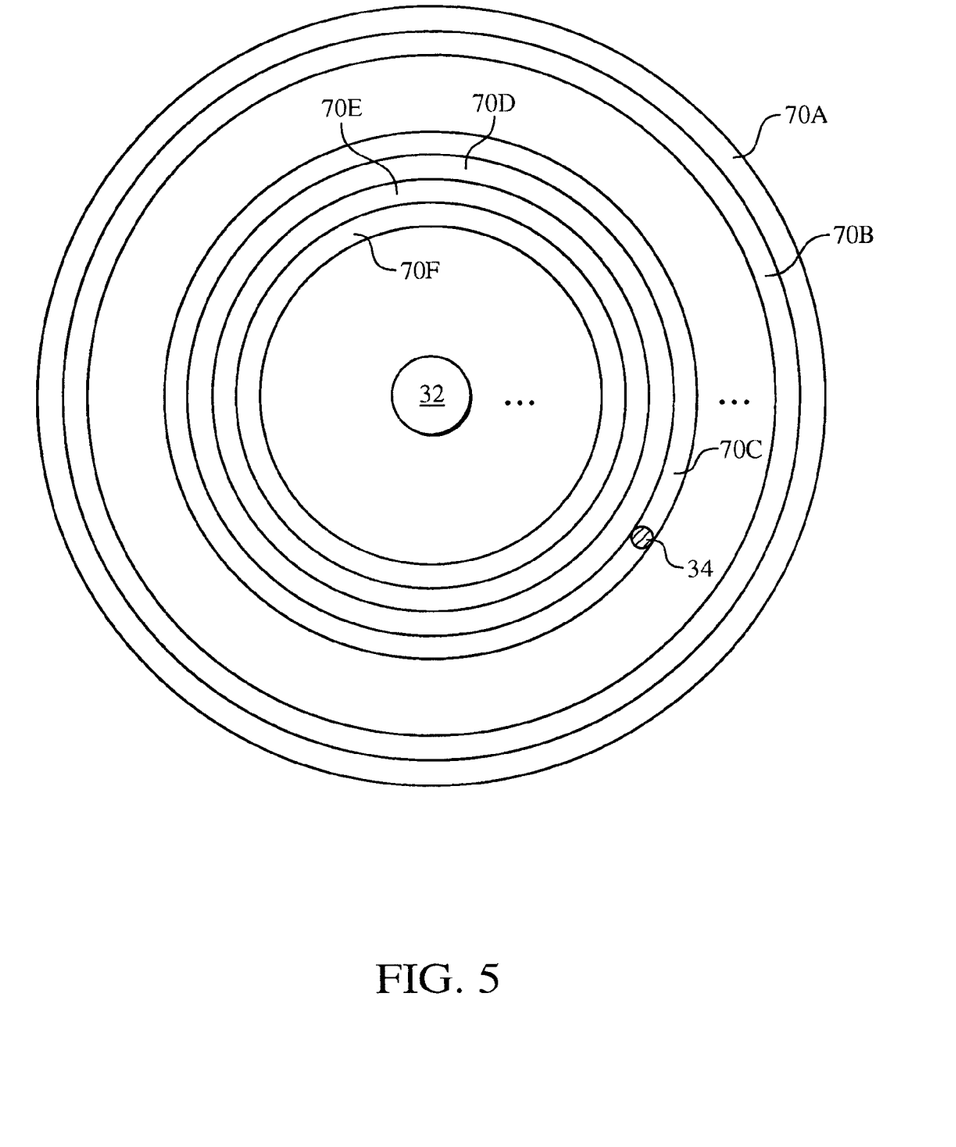
FIG. 5 is a cross-section of the spatial light distribution shown in FIG. 4.

As suggested by FIG. 4, re-entrant light 66 tends to re-enter the lumen along concentric annular regions 70A-F that are radially separated from the specularly reflected light 62. Each re-entrant such annular region 70C, best seen in FIG. 5, is a region through which light scattered from a particular depth within the wall 14 is most likely to re-enter the lumen 68. Light that has penetrated only superficially into the wall 14 before being scattered generally re-enters the lumen 68 through the innermost 70D-F such annular regions. Light that has penetrated more deeply into the wall 14 before being scattered tends to re-enter the lumen 68 through one of the outer re-entrant zones 70A-B.

FIGS. 4-5 indicate that to collect deeply-scattered light, it is desirable to collect light from a collection spot 34 that lies in an annular region 70C that is relatively far from the illumination spot 32. One way to achieve this is to extend the separation distance between the delivery mirror 60 and the collection mirror 82. However, doing so results in a longer tip assembly 30. As an alternative, the delivery mirror 60 can be angled relative to the collection mirror 82, as shown in FIG. 6.

Figure 6:
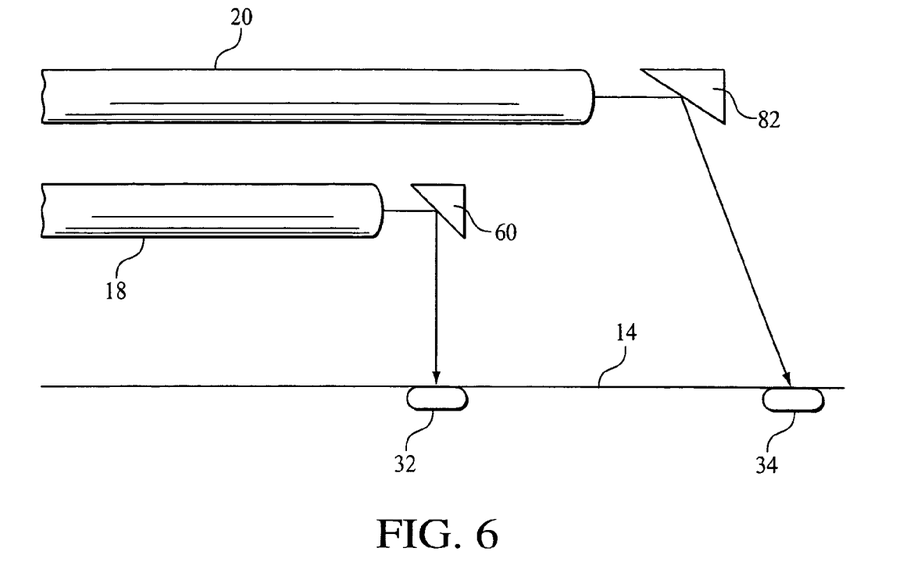
FIGS. 6-10 are schematics of different embodiments of beam redirectors.

In FIG. 6, the delivery mirror 60 is oriented to direct light radially away from the catheter, thereby delivering that light to an illumination spot 32 directly under the mirror 60. The collection mirror 82, however, is angled to collect light from a collection spot 34 that is further from the illumination spot 32 than the separation distance between the collection mirror 82 and the delivery mirror 60.

Figure 7:
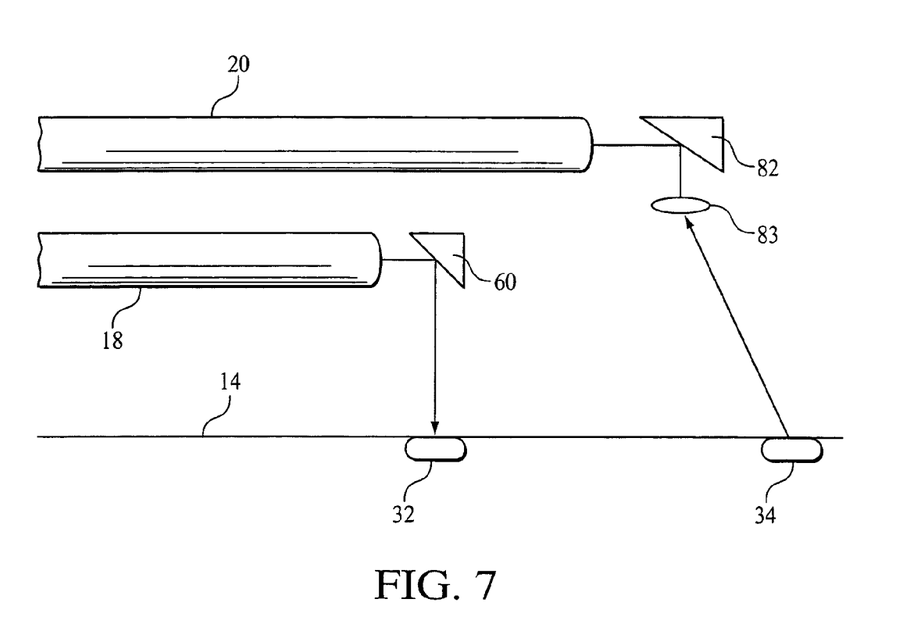

The collection spot 34 and the illumination spot 32 can be made further apart in ways other than by orienting the collection mirror 82. For example, in FIG. 7, a refracting system 83 in the optical path between the collection fiber 20 and the collection spot 34 causes the collection spot 34 to be further from the illumination spot 32 than the separation distance between the collection mirror 82 and the delivery mirror 60. Other optical elements, such as a diffracting system, can be used in place of a refracting system 83. The refracting system 83 can be a discrete lens, as shown in FIG. 7, a collection of lenses, or a lens integrally formed with the collection fiber 20.

Figure 8:
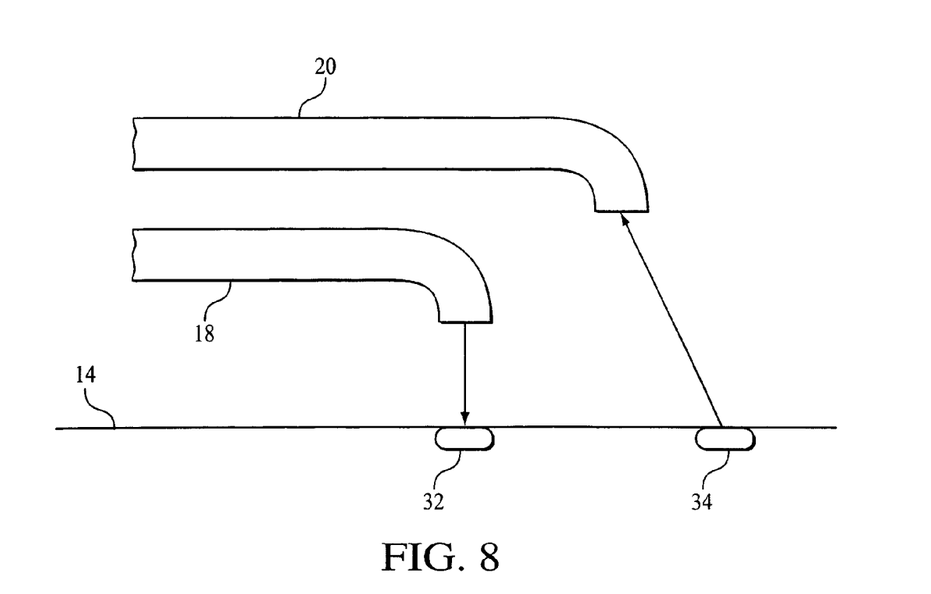

Alternatively, either the collection spot 34, the illumination spot 32, or both, can be shifted relative to each other by bending the collection fiber 20 and the delivery fiber 18, as shown in FIG. 8.

Figure 9:
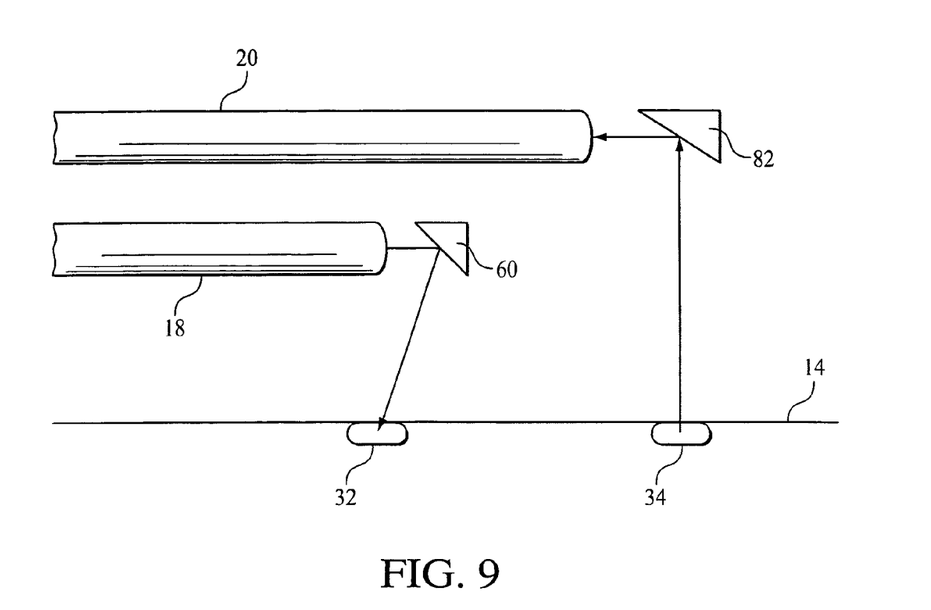
Figure 10:
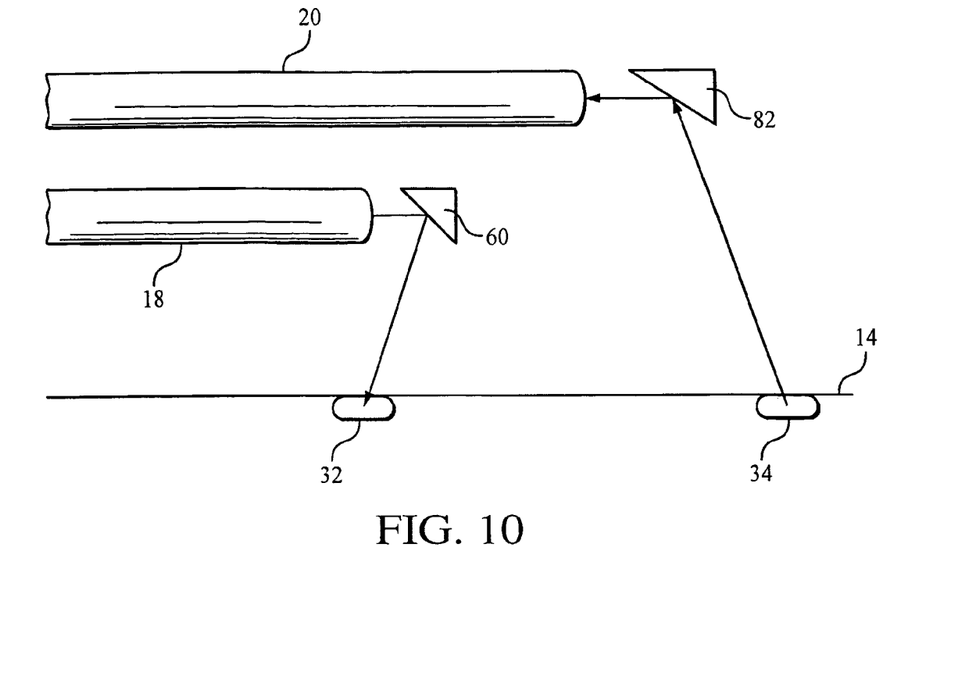

Separation of the collection spot 34 and the illumination spot 32 can also be achieved by orienting the delivery mirror 60, as shown in FIG. 9, or by orienting both the delivery mirror 60 and the collection mirror 82, as shown in FIG. 10. In both FIGS. 9 and 10, the movement of the illumination spot 32 can be achieved using a refracting system 83, by using a diffracting system, or by bending the fibers 18, 20 as described above.

In all the foregoing cases, there exists a delivery-beam redirector, through which light leaves the catheter, and a collection-beam redirector, through which scattered light enters the catheter. Whether the beam redirectors are mirrors, lenses, or ends of a bent fiber, the fact remains that they will be spatially separated from each other.

FIGS. 6-10 show embodiments in which there is only one collection fiber 20 and one delivery fiber 18. However, a catheter can also have several collection fibers 20 and/or several delivery fibers 18, each with its associated beam-redirecting element. The beam re-directing elements associated with different delivery fibers and/or collection fibers are oriented at different angles to permit collection of light from different depths. In embodiments having multiple collection and/or delivery fibers, the spacing between fibers is between 50 and 2500 micrometers. The beam re-directing elements are oriented at angles separated by one-fourth of the numerical aperture of the fiber having the smallest numerical aperture.

For a particular choice of fibers, the distance between the illumination spot 32 and the collection spot 34 determines the average penetration depth of light incident on the collection mirror 82. This distance depends on two independent variables: the distance separating the collection mirror 82 and the delivery mirror 60; and the angular orientation of the collection mirror 82 relative to that of the delivery mirror 60. For the geometry shown in FIG. 12, the contour plot of FIG. 11 shows the relationship between the average penetration depth of light received at the collection mirror 82, the separation between the collection fiber 20 and the delivery fiber 18 and the angle θ as shown in FIG. 12.

Figure 12:
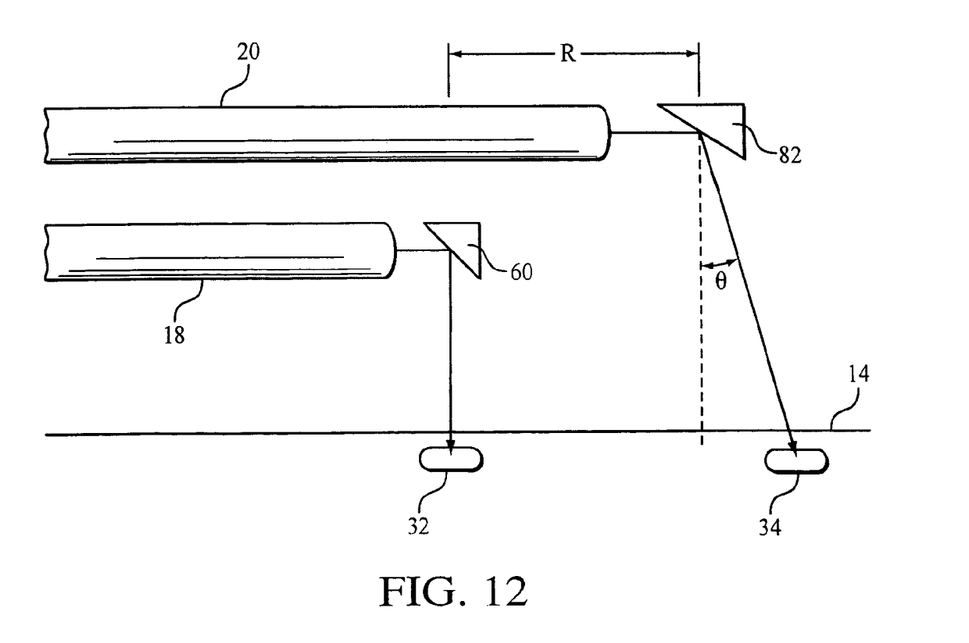
FIG. 12 is a schematic of a pair of beam redirectors for generating the contour plot of FIG. 11.

In FIG. 12, a delivery mirror 60 is oriented to direct an illumination beam radially away from the catheter. A collection mirror 82 is oriented at an angle θ relative to a line normal to the wall 14. Positive values of θ are those in which the collection mirror 82 is oriented to receive light from a collection spot 34 that is closer to the illumination spot 32 than the separation between the collection-beam redirector and the delivery-beam redirector. Conversely, negative values of θ, such as that shown in FIG. 12, are those in which the collection mirror 82 is oriented to receive light from a collection spot 34 that is further from the illumination spot 32 than the separation between the collection mirror 82 and the delivery mirror 60.

Figure 11:
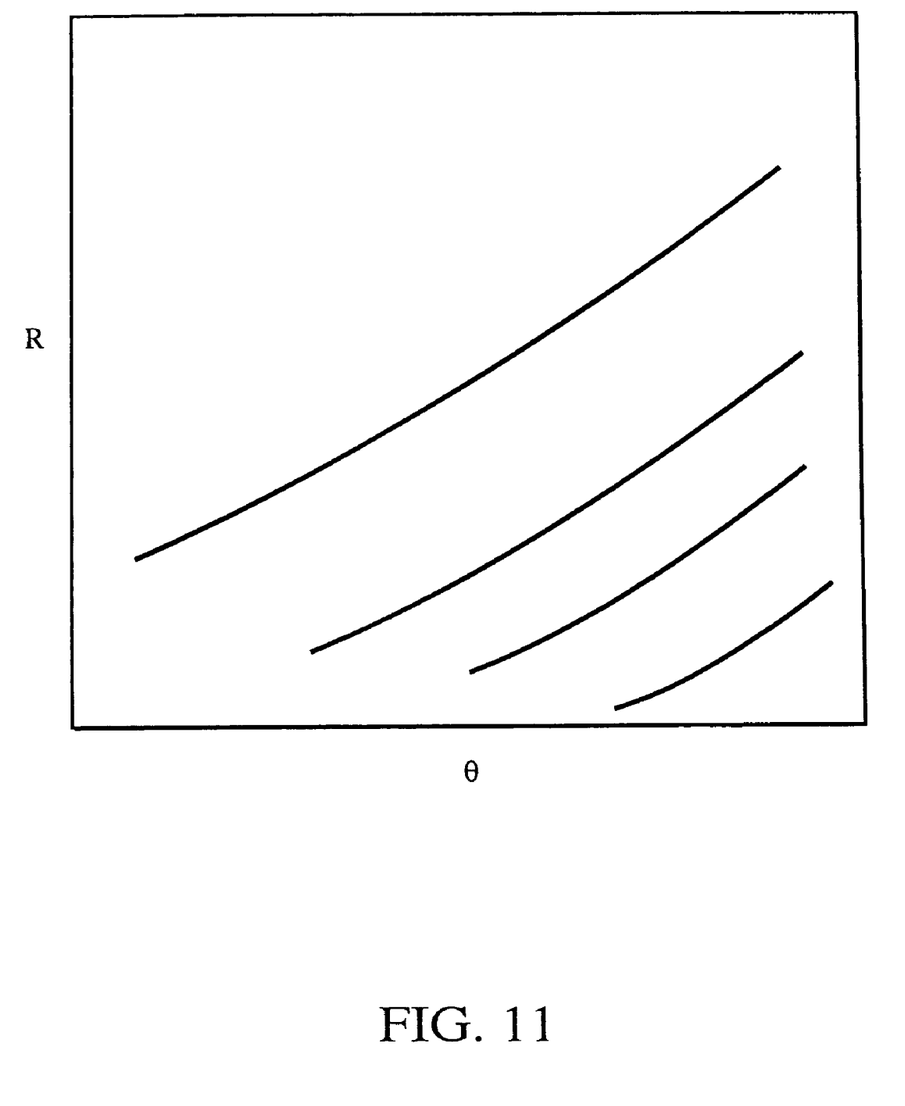
FIG. 11 is a contour plot of mean penetration depth as a function of separation and orientation of beam redirectors.

It is apparent from FIG. 11 that for a given separation between the collection mirror 82 and the delivery mirror 60, one can collect light from deeper within the wall 14 by increasing the angle θ in the negative direction. This makes possible the collection of light scattered from deep inside the wall 14 without necessarily increasing the separation between the collection mirror 82 and the delivery mirror 60. As a result, the tip assembly 30 can be made smaller without necessarily compromising the ability to detect light scattered from deep inside the wall 14. A suitable choice for the angle θ (also referred to as the pitch angle), depends on the numerical apertures of the collection fiber and the delivery fiber. One suitable choice is that in which the angle θ is the sum of the arcsines of the numerical apertures.

FIGS. 11 and 12 are discussed in the context of mirrors as collection and delivery-beam redirectors. However, it will be apparent that similar principles apply to other types of collection-beam redirectors, such as those disclosed herein.

In addition, in the discussion of FIGS. 11 and 12, only the angle of the collection mirror 82 is changed. However, similar effects can be achieved by properly orienting the delivery mirror 60, or by orienting both the delivery and collection mirrors 60, 82 together.

In some embodiments, the radian angle included between the longitudinal axes of the delivery and collection fibers 18, 20 (hereafter referred to as the "pitch angle") is between 0 radians and π radians. In this case, the axial separation between the delivery fiber and the collection fiber 18, 20 is slightly greater than the average fiber diameter but less than 3 millimeters. As used herein, "slightly greater than" means "approximately 0.1 millimeters greater than," and "average fiber diameter" means the average of the diameters of the collection fiber 20 and the delivery fiber 18.

In other embodiments, the pitch angle is between π/2 and the smaller of the numerical apertures of the delivery fiber 18 and the collection fiber 20. In this case, the axial separation between the delivery fiber 18 and the collection fiber 20 is slightly greater than the average fiber diameter but less than 1.5 millimeters.

In other embodiments, the pitch angle is within a 0.5 radian window having a lower bound defined by the greater of the numerical apertures of the delivery fiber 18 and the collection fiber 20. In this case, the axial separation distance between the delivery fiber 18 and the collection fiber 20 is within a 0.5 millimeter window having a lower bound defined by a distance slightly greater than the average fiber diameter.

In yet other embodiments, the pitch angle is within a 0.1 radian window centered at the sum of the numerical apertures of the collection and delivery fiber 18. In this case, the axial separation between the delivery and collection fibers 18, 20 is within a 0.1 millimeter interval having a lower bound that is 0.35 millimeters greater than the average fiber diameter.

Additional embodiments include those in which the pitch angle is between 0 and $\pi/2$ radians and the axial separation between the delivery and collection fibers 18, 20 is between 0.25 millimeters and 3 millimeters; those in which the pitch angle is between 0.12 radians and $\pi/2$ radians and the axial separation between the delivery and collection fibers 18, 20 is between 0.25 millimeters and 1.5 millimeters, and those in which the pitch angle is between 0.25 and 0.75 radians and the axial separation between the delivery and collection fibers 18, 20 is between 0.25 millimeters and 0.75 millimeters.

Suitable fibers for use as a delivery fiber 18 include those having a numerical aperture of 0.12 radians and core diameters of 9 micrometers, 100 micrometers, and 200 micrometers. Suitable fibers for use as a collection fiber 20 include those having a numerical aperture of 0.22 radians and core diameters of 100 micrometers or 200 micrometers. Also suitable for use as a collection fiber 20 are fibers having a numerical aperture of 0.275 radians and a core diameter of 62.5 micrometers.

The surfaces of the delivery and collection mirrors 60, 82 can be coated with a reflective coating, such as gold, silver or aluminum. These coatings can be applied by known vapor deposition techniques. Alternatively, for certain types of plastic, a reflective coating can be electroplated onto those surfaces. Or, the plastic itself can have a reflective filler, such as gold or aluminum powder, incorporated within it.

The optical bench 48 is manufactured by injection molding a plastic into a mold. In addition to being simple and inexpensive, the injection molding process makes it easy to integrate the elements of the optical bench 48 into a single monolith and to fashion structures having curved surfaces. Examples of suitable plastics include liquid crystal polymers (LCPs), polyphenylsulfone, polycarbonate, acrylonitrile butadiene-styrene ("ABS"), polyamide ("NYLON"), polyethersulfone, and polyetherimide. Alternatively, the optical bench can be manufactured by micro-machining plastic or metal, by lithographic methods, by etching, by silicon optical bench fabrication techniques, or by injection molding metal. Materials other than plastics can be used to manufacture the housing 54 and the optical bench 48. Such materials include metals, quartz or glass, and ceramics.

The floor 56 in the illustrated embodiment is integral to the housing 54. However, the floor 56 can also be made part of the optical bench 48.

As described herein, the housing 54 and the optical bench 48 are manufactured separately and later joined. However, the housing 54 and the optical bench 48 can also be manufactured together as a single unitary structure.

Using the Catheter

In use, the distal tip assembly 30 is inserted into a blood vessel, typically an artery, and guided to a location of interest. Light is then directed into the delivery fiber 18. This light exits the delivery fiber 18 at its distal tip, reflects off the delivery mirror 60 in a direction away from the plane containing the delivery and collection fibers 18, 20, and illuminates an illumination spot 32 on the wall of the artery. Light penetrating the arterial wall 14 is then scattered by structures within the wall. Some of this scattered light re-enters the blood vessel and impinges on the plane and onto the collection mirror 82. The collection mirror 82 directs this light into the collection fiber 20.

Alternatively, light incident on the wall 14 can stimulate fluorescence from structures on or within the wall 14. The portion of this fluorescent light that is incident on the collection mirror 82 is directed into the collection fiber 20.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A spectroscope comprising:
   first and second fibers, one of which defines a longitudinal axis;
   a first fixed beam-redirector in optical communication with the first fiber, the first beam-redirector being oriented to illuminate a first area having a center;
   a second fixed beam-redirector in optical communication with the second fiber and axially separated along the longitudinal axis from the first beam-redirector by a first separation distance, the second beam-redirector being oriented to illuminate a second area having a center axially separated from the center of the first area along the longitudinal axis by a second separation distance that exceeds the first separation distance by a fixed amount.

2. The spectroscope of claim 1, wherein the first beam-redirector comprises a mirror.

3. The spectroscope of claim 1, wherein the first beam-redirector comprises a lens system.

4. The spectroscope of claim 3, wherein the first beam-redirector further comprises a mirror in optical communication with the lens system.

5. The spectroscope of claim 1, wherein the first beam-redirector comprises a distal portion of the first fiber, the distal portion being bent to illuminate the first area.

6. The spectroscope of claim 1, wherein the first beam-redirector comprises a diffracting element.

7. The spectroscope of claim 1, wherein the extent to which the second separation distance exceeds the first separation distance is chosen to enhance collection of light scattered from a target located at a selected distance from the first area.

8. The spectroscope of claim 1, further comprising a catheter through which the first and second fibers extend.

9. The spectroscope of claim 1, wherein
   the first and second beam re-directors are oriented to define a pitch angle therebetween, the pitch angle being between 0 radians and $\pi$ radians; and wherein
   the first separation distance is slightly greater than an average fiber diameter but less than 3 millimeters.

10. The spectroscope of claim 1, wherein
    the first and second beam re-directors are oriented to define a pitch angle therebetween, the pitch angle being between $\pi/2$ radians and the smaller of the numerical apertures of the first and second fibers; and wherein
    the first separation distance is slightly greater than an average fiber diameter but less than 1.5 millimeters.

11. The spectroscope of claim 1, wherein
    the first and second beam re-directors are oriented to define a pitch angle therebetween, the pitch angle being within a 0.5 radian window having a lower bound defined by the greater of the numerical apertures of the first and second fibers; and wherein the first separation distance is within a 0.5 millimeter window having a lower bound defined by a distance slightly greater than an average fiber diameter.

12. The spectroscope of claim 1, wherein
the first and second beam re-directors are oriented to define a pitch angle therebetween, the pitch angle being within a 0.1 radian window centered at the sum of the numerical apertures of the first and second fibers; and wherein
the first separation distance is within a 0.1 millimeter interval having a lower bound that is 0.35 millimeters greater than an average fiber diameter.

13. The spectroscope of claim 1, wherein
the first and second beam re-directors are oriented to define a pitch angle therebetween, the pitch angle being between 0 and $\pi/2$ radians; and wherein
the first separation distance is between 0.25 millimeters and 3 millimeters.

14. The spectroscope of claim 1, wherein
the first and second beam re-directors are oriented to define a pitch angle therebetween, the pitch angle being between 0.12 radians and $\pi/2$ radians; and wherein
the first separation distance is between 0.25 millimeters and 1.5 millimeters.

15. The spectroscope of claim 1, wherein
the first and second beam re-directors are oriented to define a pitch angle therebetween, the pitch angle being between 0.25 and 0.75 radians; and wherein
the first separation distance is between 0.25 millimeters and 0.75 millimeters.

16. The spectroscope of claim 1, wherein at least one of the first and second fibers comprises an optical fiber having a numerical aperture of 0.12 radians and a core diameter selected from the group consisting of 9 micrometers, 100 micrometers, and 200 micrometers.

17. The spectroscope of claim 1, wherein at least one of the first and second fibers comprises an optical fiber having a numerical aperture of 0.22 radians and a core diameter selected from the group consisting of 100 micrometers or 200 micrometers.

18. The spectroscope of claim 1, wherein at least one of the first and second fibers comprises an optical fiber having a numerical aperture of 0.275 radians and a core diameter of 62.5 micrometers.

19. A method for collecting light scattered from behind an arterial wall, the method comprising:
providing an illumination beam redirector and a collection beam redirector axially separated from each other by a first distance along a longitudinal axis;
illuminating an illumination spot on the arterial wall, the illumination spot having a center;
pointing a collection-beam redirector toward a collection spot, the collection spot having a center axially separated along the longitudinal axis from the center of the illumination spot by a second distance that exceeds the first distance by a fixed amount; and
recovering scattered light incident on the collection-beam redirector.

20. The method of claim 19, wherein pointing a collection-beam redirector comprises orienting a collection mirror to receive light from the collection spot.

21. The method of claim 19, wherein pointing a collection beam redirector comprises providing a lens to direct light received from the collection spot.

22. The method of claim 19, wherein pointing a collection beam redirector comprises orienting an end of an optical fiber to receive light from the collection spot.

23. The method of claim 19, wherein pointing a collection beam redirector comprises:
selecting a depth from which to collect the scattered light; and
pointing the collection-beam redirector in a direction that enhances the amount of light received from the selected depth.

24. A method for collecting light scattered from behind an arterial wall, the method comprising:
providing an illumination beam redirector and a collection beam redirector axially separated from each other by a first distance along a longitudinal axis;
pointing the collection-beam redirector at a collection spot on the wall;
pointing the delivery-beam redirector toward an illumination spot on the wall in a direction away from the collection spot;
passing light through the delivery-beam redirector; and
recovering scattered light incident on the collection-beam redirector
wherein a center of the collection spot and a center of the illumination spot are axially separated from each other along the longitudinal axis by a second distance that exceeds the first distance by a fixed amount.

25. The method of claim 24, wherein pointing a delivery-beam redirector comprises orienting a delivery mirror to direct light toward the illumination spot.

26. The method of claim 24, wherein pointing a delivery-beam redirector comprises providing a lens to direct light toward the illumination spot.

27. The method of claim 24, wherein pointing a delivery-beam redirector comprises orienting an end of an optical fiber to direct light toward the illumination spot.

28. The method of claim 24, wherein pointing a delivery-beam redirector comprises:
selecting a depth from which to collect the scattered light; and
pointing the delivery-beam redirector in a direction that enhances the amount of light received from the selected depth.

29. A spectroscope comprising:
first and second fibers, one of which defines a longitudinal axis;
a first fixed beam-redirector in optical communication with the first fiber, the first beam-redirector being oriented to illuminate a first area;
a second fixed beam-redirector in optical communication with the second fiber the second beam-redirector being oriented to illuminate a second area axially separated from the first area along the longitudinal axis by an axial separation distance that increases with distance from the spectroscope.

* * * * *

UNITED STATES PATENT AND TRADEMARK OFFICE
CERTIFICATE OF CORRECTION

| | | |
|---|---|---|
| PATENT NO. | : 7,426,410 B2 | Page 1 of 1 |
| APPLICATION NO. | : 10/456979 | |
| DATED | : September 16, 2008 | |
| INVENTOR(S) | : Zuluaga et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 677 days Delete the phrase "by 677 days" and insert -- by 928 days --

Signed and Sealed this

Fourth Day of May, 2010

David J. Kappos
*Director of the United States Patent and Trademark Office*